(12) United States Patent
Ahn et al.

(10) Patent No.: US 11,015,164 B2
(45) Date of Patent: May 25, 2021

(54) CELL PRINTING APPARATUS FOR HEAT-SENSITIVE CELL PRINTING COMPOSITION

(71) Applicants: T&R BIOFAB CO., LTD., Gyeonggi-do (KR); Korea Polytechnic University Industry Academic Cooperation Foundation, Gyeonggi-do (KR)

(72) Inventors: Geunseon Ahn, Gyeonggi-do (KR); Jinhyung Shim, Gyeonggi-do (KR); Kyunghyun Min, Gyeonggi-do (KR); Wonsoo Yun, Gyeonggi-do (KR); Songwan Jin, Gyeonggi-do (KR)

(73) Assignees: T&R BIOFAB CO., LTD., Gyeonggi-do (KR); KOREA POLYTECHNIC UNIVERSITY INDUSTRY ACADEMIC COOPERATION FOUNDATION, Gyeonggi-do (KR)

( * ) Notice: Subject to any disclaimer, the term of this patent is extended or adjusted under 35 U.S.C. 154(b) by 222 days.

(21) Appl. No.: 16/029,016

(22) Filed: Jul. 6, 2018

(65) Prior Publication Data
US 2018/0312796 A1   Nov. 1, 2018

Related U.S. Application Data

(63) Continuation of application No. PCT/KR2017/000140, filed on Jan. 5, 2017.

(30) Foreign Application Priority Data

Jan. 7, 2016 (KR) .................. 10-2016-0002008
Dec. 15, 2016 (KR) .................. 10-2016-0171709

(51) Int. Cl.
C12M 1/02 (2006.01)
C12M 3/00 (2006.01)
(Continued)

(52) U.S. Cl.
CPC ............. *C12M 41/24* (2013.01); *B33Y 30/00* (2014.12); *C12M 21/08* (2013.01); *C12M 29/06* (2013.01); *C12M 33/00* (2013.01); *C12M 47/20* (2013.01)

(58) Field of Classification Search
CPC .... C12M 41/24; B29C 64/295; B29C 64/118; B29C 64/106
See application file for complete search history.

(56) References Cited

U.S. PATENT DOCUMENTS

2013/0026683 A1    1/2013  Ng et al.
2015/0314532 A1*  11/2015  Gordon ............... B29C 64/386
                                                    264/401
(Continued)

FOREIGN PATENT DOCUMENTS

EP     3 401 397 A1    11/2018
KR   10-0740228 B1    7/2007
(Continued)

OTHER PUBLICATIONS

Cui, X. et al., "Direct Human Cartilage Repair Using Three-Dimensional Bioprinting Technology," Tissue Engineering: Part A, vol. 11-12: 9 pages (2012).
(Continued)

*Primary Examiner* — Jacob T Minskey
*Assistant Examiner* — Virak Nguon
(74) *Attorney, Agent, or Firm* — Nelson Mullins Riley & Scarborough LLP; Kongsik Kim, Esq.

(57) ABSTRACT

A cell printing apparatus of the present disclosure comprises a nozzle configured to discharge a heat-sensitive cell print-
(Continued)

ing composition; and a heating unit for transferring heat to the upper side of the heat-sensitive cell printing composition which is discharged from the nozzle to be laminated. A predetermined space is formed between the heating unit and the nozzle so that the heating unit does not contact with the nozzle.

7 Claims, 3 Drawing Sheets

(51) Int. Cl.
*B33Y 30/00* (2015.01)
*C12M 1/00* (2006.01)
*C12M 1/26* (2006.01)

(56) References Cited

U.S. PATENT DOCUMENTS

| | | | | |
|---|---|---|---|---|
| 2016/0271874 | A1* | 9/2016 | Tsai | B29C 64/209 |
| 2016/0339642 | A1* | 11/2016 | Donovan | B29C 64/165 |
| 2017/0136700 | A1* | 5/2017 | Li | A61L 27/24 |
| 2017/0198252 | A1* | 7/2017 | Mironov | B33Y 80/00 |
| 2017/0369827 | A1* | 12/2017 | Langenfeld | C12M 33/00 |
| 2018/0200955 | A1* | 7/2018 | Hoelldorfer | B33Y 50/02 |
| 2018/0311898 | A1* | 11/2018 | Schwarzbaum | B29C 64/264 |
| 2019/0011095 | A1* | 1/2019 | Boonekamp | F21S 8/04 |

FOREIGN PATENT DOCUMENTS

| | | |
|---|---|---|
| KR | 10-0922232 B1 | 10/2009 |
| KR | 10-2010-0128565 A | 12/2010 |
| KR | 10-1346094 B1 | 12/2013 |
| WO | 2015/066705 A1 | 5/2015 |

OTHER PUBLICATIONS

Hofmann, M. "3D Printing Gets a Boost and Opportunities with Polymer Materials", American Chemical Society, (2014) pp. 382-386.

Knowlton, S. et al, "Bioprinting for cancer research", Trends in Biotechnology, Sep. 2015, vol. 33, No. 9, pp. 504-513.

Landeres, R., et al. "Rapid prototyping of scaffolds derived from thermoreversible hydrogels and tailored for applications in tissue engineering", Biomaterials, 23 (2002) pp. 4437-4447.

* cited by examiner

Related Art

CELL PRINTING APPARATUS FOR HEAT-SENSITIVE CELL PRINTING COMPOSITION

CROSS-REFERENCE TO RELATED APPLICATION

This application is a continuation of International Application No. PCT/KR2017/000140 filed on Jan. 5, 2017, which claims priority to Korean Application Nos. 10-2016-0002008 filed on Jan. 7, 2016 and 10-2016-0171709 filed on Dec. 15, 2016. The applications are expressly incorporated herein by reference.

TECHNICAL FIELD

The present invention relates to a cell printing apparatus, and more particularly, to a cell printing apparatus having a heating module for properly laminating a heat-sensitive cell printing composition which is discharged from a nozzle for fabricating a 3D structure.

BACKGROUND

There has been a lot of studies for fabricating tissue structures by 3D bio-printing technique. The technique is referred to as "cell printing" where a cell printing composition (10) such as collagen, gelatin, alginate or dECM which contains cells (1) and is in a gel state (2), is discharged from a nozzle of a 3D bio-printer to be printed. Collagen, gelatin, alginate, dECM and the like are generally referred to as "bio ink."

In this specification, the term "cell printing composition" means a liquid substance such as collagen, gelatin, alginate, dECM and the like which contains cells and is discharged for the purpose of 3D cell printing.

FIG. 3 is a schematic view of the cell printing apparatus of a prior art and shows the printing process according to the apparatus.

The cell printing composition (10) in a container (100) is discharged outwardly from a nozzle (150). The nozzle (150) is supported by a head unit (200), and is movable three-dimensionally (A, B and C directions) by a driving device (not illustrated).

The cell printing composition is maintained in a liquid state at a temperature lower than a first temperature, but is cured at a second temperature or higher, the second temperature being higher than the first temperature.

In the event that the cell printing composition is discharged from the nozzle (150) and is laminated on a bottom (300), non-cured layers of the cell printing composition can slip down, thereby collapsing laminated structure if the temperature of the cell printing composition is lower than the second temperature. Therefore, there is a problem in that the cell printing cannot fabricate a desired 3D structure.

In order to solve the problem, a bottom heating unit (400) is provided under a bottom (300) on which the structure is laminated so that the cell printing composition on the bottom is heated to the second temperature or higher for curing.

The conventional method has a problem in that as the layers of the structure are laminated more and more, the upper layers of the cell printing composition cannot be properly cured since the upper layers becomes far from the bottom (300) and heat is not properly transferred to the upper layers from the bottom heating unit (400).

SUMMARY

The object of the present disclosure is to provide a cell printing apparatus, in which a cell printing composition is quickly cured, regardless of a height of laminated layers for solving the problem of the prior arts.

To accomplish the object, a cell printing apparatus of one aspect of the present disclosure, comprises a nozzle configured to discharge a heat-sensitive cell printing composition; and a heating unit for transferring heat to the upper side of the heat-sensitive cell printing composition which is discharged from the nozzle to be laminated.

A predetermined space is formed between the heating unit and the nozzle so that the heating unit does not contact with the nozzle.

The heating unit may comprise a heat radiating lamp or a heating wire.

The heat radiating lamp may emit visible rays or infrared rays.

The heating unit may comprise a main body having a shape of a plate, and the heat radiating lamp or the heating wire is provided in the plate body.

The heating unit may have a flat surface equal to or larger than a laminated structure of the cell printing composition.

The cell printing apparatus may further comprises a containing unit for containing the cell printing composition. The containing unit is disposed in an opposite direction to the heating unit facing the laminated layer of the cell printing composition.

The heating unit may be bent from a center to a circumference towards the laminated structure of the cell printing composition.

The nozzle may penetrate the center of the heating unit.

According to the present disclosure, the cell printing apparatus can precisely print the 3D cell structure since the upper layers of the laminated cell printing composition can be quickly cured.

DETAILED DESCRIPTION

Hereinafter, the present disclosure will be described in detail with reference to the accompanying drawings.

The present disclosure specifically relates to the part for containing and discharging a cell printing composition among the various components of a cell printing apparatus, and thus other components of the cell printing apparatus which are unnecessary for describing the essential features of the present disclosure will not be described in detail herein. For example, a driving unit and a control unit of the cell printing apparatus are irrelevant to the essential features the present disclosure, and they can be carried out by the conventional arts. Particularly, the present disclosure relates to the cell printing apparatus using a heat-sensitive cell printing composition among various cell printing compositions.

Figure 1:
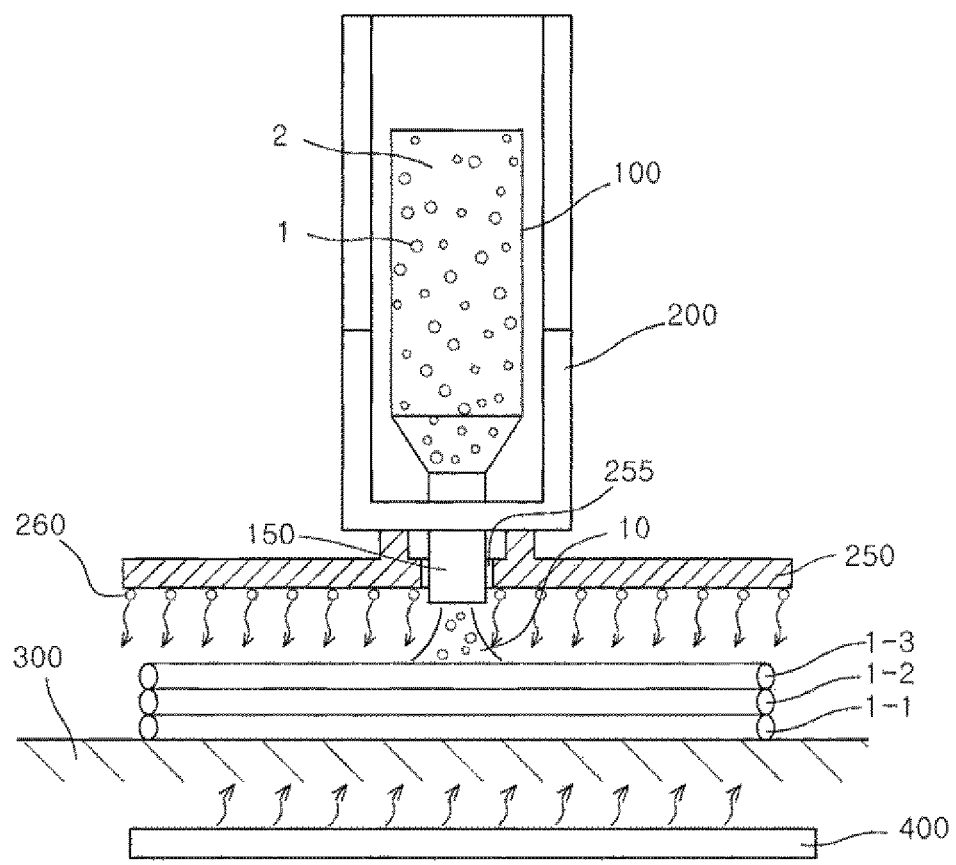
FIG. 1 is a view illustrating a cell printing apparatus according to an embodiment of the present disclosure.

FIG. 1 shows the cell printing apparatus according to an embodiment of the present disclosure. As mentioned in the above, the components which are irrelevant to the essential features of the present disclosure are not shown in FIG. 1.

The cell printing composition (10) comprises cells (1) and hydrogel (2; bio ink) such as collagen or dECM. The cell printing composition (10) is contained in a containing unit (100) and is discharged outwardly from a nozzle (150).

The nozzle (150) is supported by a head unit (200) which is movable by a driving device (not illustrated). Alternatively, a bottom (300) on which the cell printing composition (10) is laminated may be movable. The head unit (200) may be movable in one-dimensional direction, two-dimensional directions or three-dimensional directions.

A heating unit (250) provided under the head unit (200) generates heat in the downward direction and may be a heating lamp (260) such as an infrared lamp or a heating wire. It is preferred that the heating unit (250) has a shape of a plate and that the heating lamp (260) of the heating unit (250) emits visible rays and/or infrared rays. More specifically, the heating unit (250) may have a main body of a plate where the heating lamp (260) or the heating wire is provided, thereby heating the upper portion of the cell printing composition to be laminated.

Any heating lamp emitting the visible rays and/or infrared rays and any heat wire which heat the layers 1-1, 1-2 and 1-3 and the like of the cell printing composition (particularly, the uppermost layer while 3-D printing is in progress) to a gelation temperature (second temperature) or higher, can be used for the present disclosure. FIG. 1 shows three layers 1-1, 1-2 and 1-3 of the cell printing compositions, but the present disclosure is not limited thereto.

Although it is shown that the bottom (300) is provided with a bottom heating unit (400), it should be appreciated that the bottom heating unit (400) is not an essential component of the present disclosure. The bottom heating unit (400) may be a plate member which has a heating source, or may be other component capable of transferring heat to the bottom (300).

It is preferred that the heating unit (250) is disposed at an end of the nozzle (150). It is for properly transferring the heat to the uppermost layer 1-3. If the heating unit (250) can transfer the heat from the above to the layer formed by discharging the cell printing composition, the heating unit may be disposed at the head unit (200), not at the nozzle (150). Alternatively, the heating unit (250) may be disposed at other components or may be provided as a separate independent component.

It is preferred that the heating unit (250) is provided so as not to contact with the nozzle (150). As shown in FIG. 1, a predetermined space (255) is formed between the nozzle (150) and the heating unit (250). It is for preventing the cell printing composition from being cured due to heating the cell printing composition discharged from the nozzle (150) to the second temperature or higher by the heating unit (250).

The heating unit (250) may have a flat surface equal to or larger than the laminated structure of the cell printing composition as shown in FIG. 1. This structure can easily and quickly cure the laminated layers.

The containing unit (100) for containing the cell printing composition (10) is provided in the head unit (200). More specifically, the containing unit (100) is provided inside the head unit (200) at the opposite direction to the laminated layers of the cell printing composition. The containing unit (100) may be disposed outside the head unit, not inside the head unit (200).

According to the configuration of the containing unit, it can be prevented that the cell printing composition (10) contained in the containing unit is cured by the heating of the heating unit (250).

Figure 2:
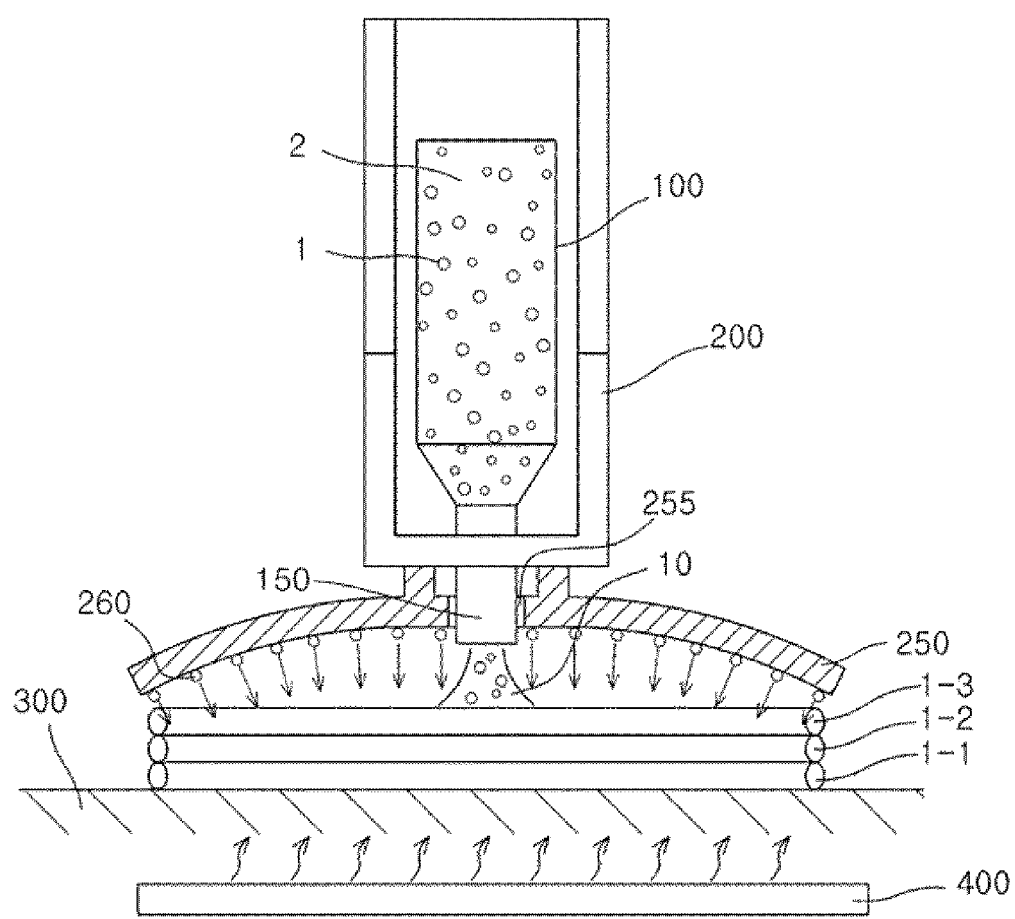
FIG. 2 is a view illustrating a cell printing apparatus according to another embodiment of the present disclosure.
Figure 3:
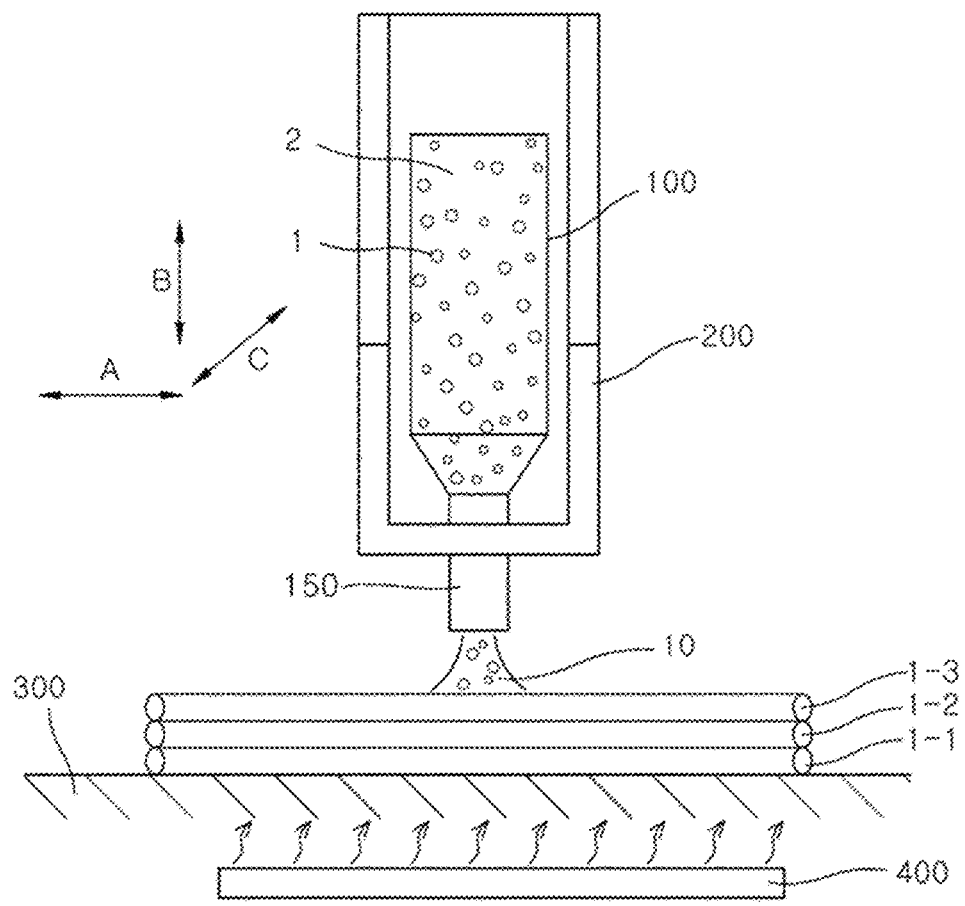
FIG. 3 is a view illustrating a cell printing apparatus of a prior art.

FIG. 2 shows a cell printing apparatus according to another embodiment of the present disclosure. The embodiment shown in FIG. 2 is substantially identical to the embodiment shown in FIG. 1, except a heating unit (250) which is bent from a center to a circumference towards the laminated structure of the cell printing composition. A nozzle (150) may penetrate the center of the heating unit (250) to discharge the cell printing composition. A predetermined space (255) may be formed between the nozzle (150) and the heating unit (250) as shown in the embodiment of FIG. 1.

According to the embodiment shown in FIG. 2, quick gelation of the cell printing composition can be accomplished since the heat applied to the laminated structure can be focused thereon. Although the heating unit (250) covers the entire laminated structure in FIG. 2, the heating unit may be smaller than the structure if it is bent from a center to a circumference towards the laminated structure. The heating unit (250) is formed as the shape of a caldron lid as shown in FIG. 2, but the heating unit may be formed in any shape if it is bent toward the laminated structure as goes to the circumference. Heating lamps (260) may be provided in the inner portion of the heating unit (250).

The operation of the cell printing apparatus of the present disclosure will be described in detail.

The cell printing composition (10) is discharged to the bottom (300) from the nozzle (150). The head unit (200) discharges the cell printing composition (10) on the bottom (300) while by a driving member moving to the place where the composition is to be laminated. The first layer 1-1 on the bottom (300) is heated to the second temperature or higher by the heating unit (250), thereby being quickly cured. If the bottom heating unit (400) is provided in the bottom (300) as in the prior art, the first layer 1-1 can be also cured by the heat transferred from the bottom heating unit (400).

When the second layer 1-2 and the third layer 1-3 are laminated on the first layer 1-1, the layers are subjected to the same process so that the cell printing composition (10) is cured. As the layers are laminated more and more, the heat transfer from the bottom heating unit 400 decreases, but the cell printing composition of the upper layer 1-3 can be quickly cured since the heat is continuously transferred from the heating unit (250) according to the present disclosure. According to the embodiment shown in FIG. 2, the heat generated by the heating unit (250) can be more focused on the laminated structure, thereby quickly curing the cell printing composition.

While the present disclosure has been described with reference to the accompanying drawings, it should be appreciated that the scope of the present disclosure is determined by the appended claims and that the scope is not limited to the embodiments and/or the drawings. It is to be appreciated that a person skilled in the art can change or modify the embodiments without departing from the scope and spirit of the present disclosure.

The present invention was supported by Priority Research Centers Program through the National Research Foundation of Korea (NRF) funded by the Ministry of Education. Science and Technology (2017R1A6A1A03015562).

The invention claimed is:
1. A cell printing apparatus comprising:
 a nozzle configured to discharge a heat-sensitive cell printing composition to create a laminated structure of the cell printing composition;
 an upper heating unit configured to transfer heat to the upper side of the heat-sensitive cell printing composition which is discharged from the nozzle to be laminated; and a bottom heating unit configured to transfer heat to the bottom side of the heat-sensitive cell printing composition, wherein the upper heating unit cures the heat-sensitive cell printing composition by heating the heat-sensitive printing composition to a predetermined temperature, wherein a predetermined space is formed between the upper heating unit and the nozzle so that the nozzle is thermally isolated from the upper heating unit, and wherein the upper heating unit has a surface which is larger than an area in the bottom of the cell printing apparatus, the area corresponding to where the laminated structure of the cell printing composition is configured to be formed.

2. The cell printing apparatus according to claim 1, wherein the upper heating unit comprises a heat radiating lamp or a heating wire.

3. The cell printing apparatus according to claim 2, wherein the heat radiating lamp emits visible rays or infrared rays.

4. The cell printing apparatus according to claim 2, wherein the upper heating unit comprises a main body having a shape of a plate, and the heat radiating lamp or the heating wire is provided in the main body.

5. The cell printing apparatus according to claim 4, wherein the upper heating unit is bent from a center to a circumference towards the laminated structure of the cell printing composition.

6. The cell printing apparatus according to claim 5, wherein the nozzle penetrates the center of the upper heating unit.

7. The cell printing apparatus according to claim 1 or 2, further comprising a containing unit for containing the cell printing composition, wherein the containing unit is disposed in an opposite direction to the upper heating unit facing the laminated layer of the cell printing composition.

* * * * *